(12) United States Patent
Guy et al.

(10) Patent No.: US 7,718,358 B2
(45) Date of Patent: May 18, 2010

(54) METHOD OF IMMUNIZATION AGAINST THE 4 DENGUE SEROTYPES

(75) Inventors: Bruno Guy, Lyons (FR); Remi Forrat, Serezin du Rhone (FR); Jean Lang, Moins (FR); Veronique Barban, Craponne (FR)

(73) Assignee: Sanofi Pasteur SA, Lyons (FR)

( * ) Notice: Subject to any disclaimer, the term of this patent is extended or adjusted under 35 U.S.C. 154(b) by 0 days.

(21) Appl. No.: 11/866,382

(22) Filed: Oct. 2, 2007

(65) Prior Publication Data

US 2008/0085288 A1 Apr. 10, 2008

Related U.S. Application Data

(60) Provisional application No. 60/867,312, filed on Nov. 27, 2006.

(30) Foreign Application Priority Data

Oct. 4, 2006 (FR) .................. 06 08660

(51) Int. Cl.
*C12Q 1/70* (2006.01)
*A61K 39/12* (2006.01)

(52) U.S. Cl. .................. 435/5; 424/201.1; 424/218.1

(58) Field of Classification Search ................ None
See application file for complete search history.

(56) References Cited

U.S. PATENT DOCUMENTS

| 6,638,514 B1 | 10/2003 | Eckels et al. |
|---|---|---|
| 2004/0192631 A1 | 9/2004 | Xiang et al. |
| 2004/0259224 A1 | 12/2004 | Guirakhoo |
| 2008/0014219 A1 | 1/2008 | Barban et al. |
| 2008/0131460 A1 | 6/2008 | Guy et al. |

FOREIGN PATENT DOCUMENTS

| EP | 1159968 A1 | 12/2001 |
|---|---|---|
| WO | WO 99/61916 | 12/1999 |
| WO | WO 00/57910 A1 | 10/2000 |
| WO | WO 01/21811 | 3/2001 |
| WO | WO 01/91790 | 12/2001 |
| WO | WO 03/101397 A2 | 12/2003 |
| WO | 01/60847 A1 | 8/2007 |

OTHER PUBLICATIONS

Whitehead et al. Nature Review Microbiology, Jul. 2007, 5:519-528.*
Shresta et al. J. Virology, Oct. 2006, 80(20):10208-10217.*
Zhou, Hao, et al., "Sculpting the Immunological Response to Dengue Fever by Polytopic Vaccination," Vaccine, 2006, pp. 2451-2459, vol. 24.
Rothman, Alan L., et al., "Induction of T Lymphocyte Responses to Dengue Virus by a Candidate Tetravalent Live Attenuated Dengue Virus Vaccine," Vaccine, 2001, pp. 4694-4699, vol. 19.
Bhamarapravati, N., et al., "Live Attenuated Tetravalent Dengue Vaccine," Vaccine, 2000, pp. 44-47, vol. 18.
Halstead, Scott B. et al., "Studies on the Immunization of Monkeys Against Dengue," The American Journal of Tropical Medicine and Hygiene, 1973, pp. 375-381, vol. 22, No. 3.
Guirakhoo, F. et al., "Safety and Efficacy of Chimeric Yellow Fever-Dengue Virus Tetravalent VaccineFormulations in Nonhuman Primates," Journal of Virology, May 2004, pp. 4761-4775, vol. 78, No. 9.
Guirakhoo et al., "Construction Safety and Immunogenicity non-human of a chimeric yellow fever-dengue virus tetravalent vaccine", Journal of Virology—The American Society for Microbiology, 2001, 75(16), 7290-7304.
Blaney, J. E., "Development of a live attenuated dengue virus vaccine using reverse genetics", Viral Immunology, 2006, 19(1), 10-32.
Sabchareon et al., "Safety and Immunogenicity of tetravalent live-attenuated dengue vaccines in Thai adult volunteers Role of serotype concentration ratio and multiple doses", American Journal of Tropical Medicine and Hygiene, 2002, 66(3), 264-272.
Guirakhoo et al., "Viremia and Immunogenicity in Nonhuman Primates of a Tetravalent Yellow Fever Dengue Chimeric Vaccine Genetic Reconstructions, Dose Adjustment and Antibody Responses Against Wild-Type Dengue Virus Isolates", Virology, 2002, 298(1), 146-159.
Halstead et al., "Studies on the Immunization of Monkeys Against Dengue I. Protection Derived from Single and Sequential Virus Infections", The Journal of Tropical Medicine and Hygiene, 1973, 22(3), 365-374.
Halstead, S.B. et al.: Protection Derived from Single Sequential Virus Infections, Journal of Tropical Medicine & Hygiene, 1973, pp. 365-374, vol. 22, No. 3.
Non-Final Office Action issued for U.S. Appl. No. 11/944,311, mailed on Jun. 15, 2009.
Final Office Action issued for U.S. Appl. No. 11/776,816, mailed on Jun. 15, 2009.

* cited by examiner

*Primary Examiner*—Stacy B Chen
(74) *Attorney, Agent, or Firm*—McDonnell Boehnen Hulbert & Berghoff LLP

(57) ABSTRACT

The invention relates to a method for inducing a protection against the 4 dengue serotypes in a patient, comprising
(a) a first series of administrations (i) of a dose of a vaccinal dengue virus of a first serotype and of a dose of a vaccinal dengue virus of a second serotype, and (ii) of a dose of a vaccinal dengue virus of a third serotype and of a dose of a vaccinal dengue virus of a fourth serotype, and
(b) a second series of administrations of doses (i) and (ii), in which the doses (i) and (ii) are administered simultaneously at separate anatomical sites, and
in which the second series (b) is implemented at least 30 days to at most 12 months after the first series (a).

13 Claims, No Drawings

SEQUENCE LISTING

<160> NUMBER OF SEQ ID NOS: 2

<210> SEQ ID NO 1
<211> LENGTH: 10735
<212> TYPE: DNA
<213> ORGANISM: Dengue virus

<400> SEQUENCE: 1

```
agttgttagt ctacgtggac cgacaagaac agtttcgaat cggaagcttg cttaacgtag      60
ttctaacagt tttttattag agagcagatc tctgatgatc aaccaacgaa aaaagacggg     120
tcgaccgtct ttcaatatgc tgaaacgcgc gagaaaccgc gtgtcaactg tttcacagtt     180
ggcgaagaga ttctcaaaag gattgctctc aggccaagga cccatgaaat tggtgatggc     240
tttcatagca ttcttaagat ttctagccat accccccaaca gcaggaattt tggctagatg     300
gggctcattc aagaagaatg gagcgattaa agtgttacgg ggtttcaaga gagaaatctc     360
aaacatgcta aacataatga acaggaggaa aagatccgtg accatgctcc ttatgctgct     420
gcccacagcc ctggcgttcc atctgacgac acgaggggga gagccgcata tgatagttag     480
caagcaggaa agaggaaagt cacttttgtt caagacctct gcaggtgtca acatgtgcac     540
cctcattgcg atggatttgg gagagttgtg tgaggacacg atgacctaca atgcccccg      600 gatcactgag gcggaaccag atgacgttga ctgttggtgc aatgccacgg acacatgggt     660
```

```
gacctatgga acgtgctctc aaactggcga acaccgacga gacaaacgtt ccgtcgcatt      720
ggccccacac gtggggcttg gcctagaaac aagagccgaa acgtggatgt cctctgaagg      780
tgcttggaaa cagatacaaa aagtagagac ttgggctctg agacatccag gattcacggt      840
gatagccctt tttctagcac atgccatagg aacatccatc acccagaaag ggatcatttt      900
cattttgctg atgctggtaa caccatctat ggccatgcga tgcgtgggaa taggcaacag      960
agacttcgtg gaaggactgt caggagcaac atgggtggat gtggtactgg agcatggaag     1020
ttgcgtcacc accatggcaa aaaacaaacc aacactggac attgaactct gaagacgga      1080 ggtcacaaac cctgcagttc tgcgtaaatt gtgcattgaa gctaaaatat caaacaccac     1140
caccgattcg agatgtccaa cacaaggaga agccacactg gtggaagaac aagacgcgaa     1200
ctttgtgtgc cgacgaacgt tcgtggacag aggctgggc aatggctgtg ggctattcgg      1260
aaaaggtagt ctaataacgt gtgccaagtt taagtgtgtg acaaaactag aaggaaagat     1320
agctcaatat gaaaacctaa aatattcagt gatagtcacc gtccacactg gagatcagca     1380
ccaggtggga aatgagacta cagaacatgg aacaactgca accataacac ctcaagctcc     1440
tacgtcggaa atacagctga ccgactacgg aaccccttaca ttagattgtt cacctaggac     1500
agggctagat tttaacgaga tggtgttgct gacaatgaaa aagaaatcat ggcttgtcca     1560
caaacagtgg tttctagact taccactgcc ttggacctct ggggctttaa catcccaaga     1620
gacttggaac agacaagatt tactggtcac atttaagaca gctcatgcaa agaagcagga     1680
agtagtcgta ctaggatcac aagaaggagc aatgcacact cgctgactg gagcgacaga     1740 aatccaaacg tcaggaacga caacaatttt cgcaggacac ctaaaatgca gactaaaaat     1800 ggacaaaacta actttaaaag ggatgtcata tgtgatgtgc acaggctcat tcaagttaga     1860
gaaagaagtg gctgagaccc agcatggaac tgttctggtg caggttaaat atgaaggaac     1920
agacgcacca tgcaagattc ccttttcgac ccaagatgag aaaggagcaa cccagaatgg     1980
gagattaata acagccaacc ccatagtcac tgacaaagaa aaaccagtca atattgaggc     2040
agaaccaccc tttggtgaga gctacatcgt ggtaggagca ggtgaaaaag ctttgaaact     2100
aagctggttc aagaaaggaa gcagcatagg gaaaatgttt gaagcaactg cccgaggagc     2160
acgaaggatg gccattctgg gagacaccgc atgggactc ggttctatag gaggagtgtt     2220
cacgtctatg ggaaaactgg tacaccaggt ttttggaact gcatatggag ttttgttag     2280 cggagtttct tggaccatga aaataggaat agggattctg ctgacatggc taggattaaa     2340
ttcaaggaac acgtcccttt cggtgatgtg catcgcagtt ggcatggtca cactgtacct     2400
aggagtcatg gttcaggcag attcgggatg tgtaatcaac tggaaaggca gagaacttaa     2460
atgtggaagc ggcattttg tcactaatga agttcacact tggacagagc aatacaaatt     2520
ccaggctgac tcccccaaga gactatcagc agccattggg aaggcatggg aggagggtgt     2580
gtgtggaatc cgatcagcca ctcgtctcga aacatcatg tggaaacaaa tatcaaatga     2640
attgaaccac atcctacttg aaaatgacat gaaatttaca gtggtcgtgg gagacgttag     2700
tggaatcttg gccaaggaa aaaaaatgat taggccacaa cccatggaac acaaatactc     2760
gtggaaaagc tggggaaaag ctaaaatcat aggagcggat gtacagaaca ccaccttcat     2820
catcgacggc ccaaacaccc cagaatgccc tgacaatcaa agagcatgga atatttggga     2880
agtagaggac tatggatttg ggattttcac gacaaacata tggttgaaat tgcgtgactc     2940
ctacacccaa gtatgtgacc accggctgat gtcagctgcc attaaggaca gcaaggcagt     3000
ccatgctgac atggggtact ggatagaaag tgaaaagaac gagacatgga gttggcgag     3060
```

-continued

```
agcctcctttt ataagaagtta agacatgcat ctggccaaaa tcccacactc tatggagcaa    3120
tggagttctg gaaagtgaaa tgataattcc aaagatatat ggaggaccaa tatctcagca    3180
caactacaga ccaggatatt tcacacaaac agcagggccg tggcacctag gcaagttgga    3240
actagatttc gattttttgtg aaggtaccac agttgttgtg gatgaacatt gtggaaatcg    3300
aggaccatct ctcagaacca caacagtcac aggaaagata atccatgaat ggtgctgcag    3360
atcttgtacg ctaccccccc tacgtttcaa aggggaagac gggtgttggt acggcatgga    3420
aatcagacca gtgaaggaca aggaagagaa cctggtcaag tcaatggtct ctgcagggtc    3480
aggagaagtg gacagctttt cactaggact gctatgcata tcaataatga ttgaagaagt    3540
gatgagatcc agatggagca aaaaaatgct gatgactgga acactggctg tgttcctcct    3600
tcttataatg ggacaattga catggagtga tctgatcagg ttatgtatta tggttggagc    3660
caacgcttca gacaagatgg ggatgggaac aacgtaccta gctttaatgg ccactttcaa    3720
aatgagacca atgttcgccg tcgggctatt atttcgcaga ctaacatcta gagaagttct    3780
tcttcttaca attggcttga gcctggtggc atccgtggag ctaccaagtt ccctagagga    3840
gctgggggat ggacttgcaa taggcatcat gatgttgaaa ttattgactg attttcagtc    3900
acaccagcta tgggctactc tgctatcctt gacatttatt aaaacaactt tttcattgca    3960
ctatgcatgg aagacaatgg ctatggtact gtcaattgta tctctcttcc ctttatgcct    4020
gtccacgacc tctcaaaaaa caacatggct tccggtgctg ttgggatctc ttggatgcaa    4080
accactaccc atgtttctta taacagaaaa caaaatctgg ggaaggaaga gttggcccct    4140
caatgaagga attatggctg ttggaatagt tagtattcta ctaagttcac ttttaaaaaa    4200
tgatgtgccg ctagccggcc cattaatagc tggaggcatg ctaatagcat gttatgtcat    4260
atccggaagc tcagctgatt tatcactgga gaaagcggct gaggtctcct gggaggaaga    4320
agcagaacac tcaggcgcct cacacaacat actagtagag gttcaagatg atggaaccat    4380
gaagataaaa gatgaagaga gagatgacac gctccaccat ctccttaaag caactctgct    4440
ggcagtctca ggggtgtacc caatgtcaat accagcgacc ctttttgtgt ggtattttg    4500 gcagaaaaag aaacagagat caggagtgct atgggacaca cccagccccc cagaagtgga    4560
aagagcagtt cttgatgatg gcatctatag aattttgcaa agaggactgt tgggcaggtc    4620
ccaagtagga gtaggagttt tccaagaagg cgtgttccac acaatgtggc acgtcactag    4680
gggagctgtc ctcatgtatc aaggaaaaag gctggaacca agctgggcca gtgtcaaaaa    4740
agacttgatc tcatatggag gaggttggag gtttcaagga tcctgaaaca cgggagaaga    4800
agtacaggtg attgctgttg aaccgggaaa aaaccccaaa aatgtacaaa caacgccggg    4860
taccttcaag acccctgaag gcgaagttgg agccatagcc ttagactta aacctggcac    4920 atctggatct cccatcgtaa acagagaggg aaaaatagta ggtctttatg gaaatggagt    4980
ggtgacaaca agcggaactt acgttagtgc catagctcaa gctaaggcat cacaagaagg    5040
gcctctacca gagattgagg acaaggtgtt taggaaaaga aacttaacaa taatggacct    5100
acatccagga tcgggaaaaa caagaagata ccttccagcc atagtccgtg aggccataaa    5160
aaggaagctg cgcacgctaa tcctagctcc cacaagagtt gtcgcttctg aaatggcaga    5220
ggcactcaag ggagtgccaa taaggtatca gacaacagca gtgaagagtg aacacacagg    5280
aaaggagata gttgacctta tgtgccacgc cactttcacc atgcgcctcc tgtctcccgt    5340
gagagttccc aattataaca tgattatcat ggatgaagca cacttcaccg atccagccag    5400
catagcagcc agagggtaca tctcaacccg agtgggtatg ggtgaagcag ctgcgatctt    5460
```

```
tatgacagcc actcccccag gatcggtgga ggccttttcca cagagcaatg caattatcca   5520
agatgaggaa agagacattc ctgagagatc atggaactga ggctatgact ggatcactga   5580
tttttccaggt aaaacagtct ggtttgttcc aagcatcaaa tcaggaaatg acattgccaa   5640
ctgtttaaga aaaacggga aacgggtgat ccaattgagc agaaaaacct ttgacactga   5700
gtaccagaaa acaaaaaaca acgactggga ctatgtcgtc acaacagaca tttccgaaat   5760
gggagcaaat ttccgggccg acagggtaat agacccaagg cggtgtctga aaccggtaat   5820
actaaaagat ggtccagagc gcgtcattct agccggaccg atgccagtga ctgtggccag   5880
tgccgcccag aggagaggaa gaattggaag gaaccaaaac aaggaaggtg atcagtatat   5940
ttacatggga cagcctttaa aaatgatga ggaccacgct cattggacag aagcaaagat   6000
gctccttgac aatataaaca caccagaagg gattatccca gccctctttg agccggagag   6060
agaaaagagt gcagctatag acggggaata cagactgcgg ggtgaagcaa ggaaaacgtt   6120
cgtggagctc atgagaagag gggatctacc agtctggcta tcctacaaag ttgcctcaga   6180
aggcttccag tactccgaca gaaggtggtg cttcgatggg gaaaggaaca ccaggtgtt   6240
ggaggagaac atggacgtgg agatctggac aaaagaagga gaaagaaaga aactacgacc   6300
tcgctggttg gacgccagaa catactctga cccactggct ctgcgcgagt ttaaagagtt   6360
tgcagcagga agaagaagcg tctcaggtga cctaatatta gaatagggaa aacttccaca   6420
acatttgacg caaagggccc agaatgcttt ggacaacttg gtcatgttgc acaattccga   6480
acaaggagga aaagcctata gacatgctat ggaagaactg ccagacacaa tagaaacgtt   6540
gatgctccta gccttgatag ctgtgttgac tggtggagtg acgctgttct tcctatcagg   6600
aagaggtcta ggaaaaacat ctatcggctt actctgcgtg atggcctcaa gcgcactgtt   6660
atggatggcc agtgtggagc cccattggat agcggcctcc atcatactgg agttctttct   6720
gatggtactg cttattccag agccagacag acagcgcact ccacaggaca accagctagc   6780
atatgtggtg ataggtctgt tattcgtgat attgacagtg gcagccaatg agatgggatt   6840
attggaaacc acaaagaaag acctggggat tggccatgta gctgctgaaa accaccacca   6900
tgctacaatg ctggacgtag acctacatcc agcttcagcc tggaccctct atgcagtggc   6960
cacaacaatc atcactccta tgatgagaca cacaattgaa acacaacggc aaatatttc   7020
cctgacagcc atcgcaaacc aagcagctat attgatggga cttgacaagg gatggccaat   7080
atcgaagatg gacataggag ttccacttct cgccttgggg tgctattccc aagtgaatcc   7140
gctgacactg atagcggcag tattgatgct agtagctcat tacgccataa ttggacctgg   7200
actgcaagca aaagctacta gagaagctca aaaaagaaca gcggctggaa taatgaaaaa   7260
tccaactgtc gacgggattg ttgcaataga cttagatccc gtggtttacg atgcaaaatt   7320
tgaaaaacag ctaggccaaa taatgttgtt gatactttgc acatcacaga ttcttttgat   7380
gcggactaca tgggccttgt gtgaatccat cacattggct actggacctc tgaccactct   7440
ttgggaggga tctccaggaa aattctggaa caccacaata gcggtatcca tggcaaacat   7500
tttcaggggga agttatctag caggagcagg tctggccttc tcattaatga atctctagg   7560
aggaggtagg agaggcacgg gagcccaagg ggaaacactg ggagaaaaat ggaaaagaca   7620
actaaaccaa ctgagcaagt cagaattcaa tacttacaag aggagtggga ttatggaggt   7680
ggatagatcc gaagccaaag agggactgaa aagaggagaa acaaccaaac acgcagtatc   7740
gagaggaacg gccaaactga ggtggttcgt ggagaggaac cttgtgaaac cagaagggaa   7800
agtcatagac ctcggttgtg gaagaggtgg ctggtcatat tattgcgctg ggctgaagaa   7860
```

```
agtcacagaa gtgaaaggat acacaaaagg aggacctgga catgaggaac caatcccaat    7920
ggcgacctat ggatggaacc tagtaaggct gcactccgga aaagatgtat tttttatacc    7980
acctgagaaa tgtgacaccc ttttgtgtga tattggtgag tcctctccga acccaactat    8040
agaggaagga agaacgttac gtgttctgaa aatggtggaa ccatggctca gaggaaacca    8100
attttgcata aaaattctaa atccctatat gccgagcgtg gtagaaactc tggaacaaat    8160
gcaaagaaaa catggaggaa tgctagtgcg aaacccactc tcaagaaatt ccacccatga    8220
aatgtactgg gtttcatgtg aacaggaaa cattgtgtca gcagtaaaca tgacatctag     8280
aatgttgcta atcggttca caatggctca caggaagcca acatatgaaa gagacgtgga     8340
cttaggcgct ggaacaagac atgtggcagt agaaccagag gtagccaacc tagatatcat    8400
tggccagagg atagagaata taaaaaatga acataagtca acatggcatt atgatgagga    8460
caatccatac aaaacatggg cctatcatgg atcatatgag gttaagccat caggatcggc    8520
ctcatccatg gtcaatggcg tggtgagatt gctcaccaaa ccatgggatg ttatccccat    8580
ggtcacacaa atagccatga ctgataccac acccttggaa caacagaggg tgtttaaaga    8640
gaaagttgac acgcgcacac caaaagcaaa acgtggcaca gcacaaatta tggaagtgac    8700
agccaggtgg ttatggggtt cctttctag aaacaaaaaa cccagaattt gcacaagaga     8760
ggagtttaca agaaaagtta ggtcaaacgc agctattgga gcagtgttcg ttgatgaaaa    8820
tcaatggaac tcggcaaaag aagcagtgga agacgaacgg ttctgggaac ttgtccacag    8880
agagagggag cttcataaac agggggaaatg tgccacgtgt gtctacaata tgatggggaa   8940
gagagagaaa aaattaggag agttcggaaa ggcaaaagga agtcgtgcaa tatggtacat    9000
gtggttggga gcacgcttcc tagagtttga agcccttggt ttcatgaatg aagatcactg    9060
gttcagtaga gagaattcac tcagtggagt ggaaggagaa ggactccaca aacttggata    9120
catactcaga gacatatcaa ggattccagg ggggaacatg tatgcagatg acacagccgg    9180
atgggacaca agaataacag aggatgatct ccagaatgag gctaaaatca ctgacatcat    9240
ggagcccgaa catgccctgc tggctacgtc aatcttttaag ctgacctacc aaaataaggt   9300
ggtaagggtg cagagaccag caaaaaatgg aaccgtgatg gatgttatat ccagacgtga    9360
ccagagaggc agtggacagg ttggaactta tggcttaaac actttcacca acatggaggc    9420
ccaactgata agacaaatgg agtctgaggg aatctttta cccagcgaat ggaaaccccc     9480
aaatctagcc ggaagagttc tcgactggtt ggaaaaatat ggtgtcgaaa ggctgaaaag    9540
aatggcaatc agcggagatg actgtgtggt gaaaccaatt gatgacaggt tcgcaacagc    9600
cttaacagct ttgaatgaca tgggaaaagt aagaaaagac ataccacaat gggaaccttc    9660
aaaaggatgg aatgattggc aacaagtgcc tttctgttca caccacttcc accagctaat    9720
tatgaaggat gggagggaga tagtggtgcc atgccgcaac caagatgaac ttgtggggag    9780
ggccagagta tcacaaggcg ccggatggag cctgagagaa accgcatgcc taggcaagtc    9840
atatgcacaa atgtggcagc tgatgtattt ccacaggaga gacctgagac tggcggctaa    9900
cgctatttgt tcagccgttc cagttgattg ggtcccaacc agccgcacca cctggtcgat    9960
ccatgcccat caccaatgga tgacaacaga agacatgtta tcagtatgga ataggtctg    10020
gatagaggaa aacccatgga tggaggataa gactcatgtg tccagttggg aagaagttcc   10080
atacctagga aagagggaag atcagtggtg tggatccctg ataggcttaa cagcaagggc   10140
cacctgggcc actaatatac aagtggccat aaaccaagtg agaaggctca ttgggaatga   10200
gaattatcta gattacatga catcaatgaa gagattcaag aatgagagtg atcccgaagg   10260
```

-continued

| | |
|---|---|
| ggcactctgg taagtcaaca cattcacaaa ataaaggaaa ataaaaaatc aaatgaggca | 10320 |
| agaagtcagg ccagattaag ccatagtacg gtaagagcta tgctgcctgt gagcccgtc | 10380 |
| caaggacgta aaatgaagtc aggccgaaag ccacggtttg agcaagccgt gctgcctgtg | 10440 |
| gctccatcgt ggggatgtaa aaacccggga ggctgcaacc catggaagct gtacgcatgg | 10500 |
| ggtagcagac tagtggttag aggagacccc tcccaagaca caacgcagca gcggggccca | 10560 |
| acaccagggg aagctgtacc ctggtggtaa ggactagagg ttagaggaga ccccccgcgt | 10620 |
| aacaataaac agcatattga cgctgggaga accagagat cctgctgtct ctacagcatc | 10680 |
| attccaggca cagaacgcca gaaaatggaa tggtgctgtt aatcaacag gttct | 10735 |

<210> SEQ ID NO 2
<211> LENGTH: 10723
<212> TYPE: DNA
<213> ORGANISM: Dengue virus

<400> SEQUENCE: 2

| | |
|---|---|
| agttgttagt ctacgtggac cgacaaagac agattctttg agggagctaa gctcaatgta | 60 |
| gttctaacag tttttttaatt agagagcaga tctctgatga ataaccaacg aaaaaggcg | 120 |
| aaaacacgc ctttcaatat gctgaaacgc gagagaaacc gcgtgtcgac tgtgcaacag | 180 |
| ctgacaaaga gattctcact tggaatgctg cagggacgag gaccattaaa actgttcatg | 240 |
| gccctggtgg cgttccttcg tttcctaaca atcccaccaa cagcagggat attgaagaga | 300 |
| tggggaacaa ttaaaaaatc aaagctatt aatgttttga gagggttcag aaagagatt | 360 |
| ggaaggatgc tgaacatctt gaataggaga cgcagatctg caggcatgat cattatgctg | 420 |
| attccaacag tgatggcgtt ccatttaacc acacgtaacg gagaaccaca catgatcgtc | 480 |
| agcagacaag agaaagggaa aagtcttctg tttaaaacag aggttggcgt gaacatgtgt | 540 |
| accctcatgg ccatggacct tggtgaattg tgtgaagaca caatcacgta caagtgtccc | 600 |
| cttctcaggc agaatgagcc agaagacata gactgttggt gcaactctac gtccacgtgg | 660 |
| gtaacttatg gacgtgtac caccatggga gaacatagaa gagaaaaag atcagtggca | 720 |
| ctcgttccac atgtgcgaat gggactggag acacgaactg aaacatggat gtcatcagaa | 780 |
| ggggcctgga acatgtcca gagaattgaa acttggatct tgagacatcc aggcttcacc | 840 |
| atgatggcag caatcctggc atacaccata ggaacgacac atttccaaag agccctgatt | 900 |
| ttcatcttac tgacagctgt cactccttca atgacaatgc gttgcatagg aatgtcaaat | 960 |
| agagactttg tggaaggggt tcaggaggaa gctgggttg acatagtctt agaacatgga | 1020 |
| agctgtgtga cgacgatggc aaaaaacaaa ccaacattgg attttgaact gataaaaaca | 1080 |
| gaagccaaac agcctgccac cctaaggaag tactgtatag aggcaaagct aaccaacaca | 1140 |
| acaacagaat ctcgctgccc aacacaaggg gaacccagcc taatgaaga gcaggacaaa | 1200 |
| aggttcgtct gcaaacactc catggtagac agaggatggg gaaatggatg tggactattt | 1260 |
| ggaaagggag gcattgtgac ctgtgctatg ttcagatgca aaaagaacat ggaaggaaaa | 1320 |
| gttgtgcaac agaaaaactt ggaatacacc attgtgataa cacctcactc aggggaagag | 1380 |
| catgcagtcg gaaatgacac aggaaaacat ggcaaggaaa tcaaaataac accacagagt | 1440 |
| tccatcacag aagcagaatt gacaggttat ggcactgtca caatgagtg ctctccaaga | 1500 |
| acgggcctcg acttcaatga gatggtgttg ctgcagatgg aaaataaagc ttggctggtg | 1560 |
| cacaggcaat ggttcctaga cctgccgtta ccatggttgc ccggagcgga cacacaagag | 1620 |
| tcaaattgga tacagaagga gacattggtc actttcaaaa atcccatgc gaagaaacag | 1680 |

```
gatgttgttg tttttaggatc ccaagaaggg gccatgcaca cagcacttac aggggccaca      1740
gaaatccaaa tgtcatcagg aaacttactc ttcacaggac atctcaagtg caggctgaga      1800
atggacaagc tacagctcaa aggaatgtca tactctatgt gcacaggaaa gtttaaagtt      1860
gtgaaggaaa tagcagaaac acaacatgga acaatagtta tcagagtgca atatgaaggg      1920
gacggctctc catgcaagat ccctttgag ataatggatt tggaaaaaag acatgtctta      1980
ggtcgcctga ttacagtcaa cccaattgtg acagaaaaag atagcccagt caacatagaa      2040
gcagaacctc catttggaga cagctacatc atcataggag tagagccggg acaactgaag      2100
ctcaactggt ttaagaaagg aagttctatc ggccaaatgt tgagacaac aatgaggggg      2160 gcgaagagaa tggccatttt aggtgacaca gcctgggatt ttggatcctt gggaggagtg      2220
tttacatcta taggaaaggc tctccaccaa gtctttggag caatctatgg agctgccttc      2280 agtgggggttt catggactat gaaaatcctc ataggagtca ttatcacatg gataggaatg      2340
aattcacgca gcacctcact gtctgtgaca ctagtattgg tgggaattgt gacactgtat      2400
ttgggagtca tggtgcaggc cgatagtggt tgcgttgtga gctggaaaaa caagaactg       2460 aaatgtggca gtgggatttt catcacagac aacgtgcaca catggacaga acaatacaaa      2520
ttccaaccag aatccccttc aaaactagct tcagctatcc agaaagccca tgaagaggac      2580
atttgtggaa tccgctcagt aacaagactg gagaatctga tgtggaaaca aataacacca      2640
gaattgaatc acattctatc agaaaatgag gtgaagttaa ctattatgac aggagacatc      2700
aaaggaatca tgcaggcagg aaaacgatct ctgcggcctc agcccactga gctgaagtat      2760
tcatggaaaa catggggcaa agcaaaaatg ctctctacag agtctcataa ccagaccttt      2820
ctcattgatg gccccgaaac agcagaatgc cccaacacaa atagagcttg gaattcgttg      2880
gaagttgaag actatggctt tggagtattc accaccaata tatggctaaa attgaaagaa      2940
aaacaggatg tattctgcga ctcaaaactc atgtcagcgg ccataaaaga caacagagcc      3000
gtccatgccg atatgggtta ttggatagaa agtgcactca atgacacatg gaagatagag      3060
aaagcctctt tcattgaagt taaaaactgc cactggccaa aatcacacac cctctggagc      3120
aatggagtgc tagaaagtga gatgataatt ccaaagaatc tcgctggacc agtgtctcaa      3180
cacaactata gaccaggcta ccatacacaa ataacaggac catggcatct aggtaagctt      3240
gagatggact ttgatttctg tgatggaaca acagtggtag tgactgagga ctgcggaaat      3300
agaggaccct ctttgagaac aaccactgcc tctggaaaac tcataacaga tggtgctgc       3360 cgatcttgca cattaccacc gctaagatac agaggtgagg atgggtgctg gtacgggatg      3420
gaaatcagac cattgaagga gaagaagag aatttggtca actccttggt cacagctgga      3480
catgggcagg tcgacaactt ttcactagga gtcttggaa tggcattgtt cctggaggaa      3540
atgcttagga cccgagtagg aacgaaacat gcaatactac tagttgcagt ttcttttgtg      3600
acattgatca cagggaacat gtcctttaga gacctgggaa gagtgatggt tatggtaggc      3660
gccactatga cggatgacat aggtatgggc gtgacttatc ttgccctact agcagccttc      3720
aaagtcagac caacttttgc agctggacta ctcttgagaa agctgacctc aaggaattg       3780 atgatgacta ctataggaat tgtactcctc tcccagagca ccataccaga gaccattctt      3840
gagttgactg atgcgttagc cttaggcatg atggtcctca aatggtgag aaatatggaa      3900 aagtatcaat ggcagtgac tatcatggct atcttgtgcg tcccaaacgc agtgatatta      3960
caaaacgcat ggaaagtgag ttgcacaata ttggcagtgg tgtccgtttc cccactgttc      4020
ttaacatcct cacagcaaaa aacagattgg ataccattag cattgacgat caaaggtctc      4080
```

```
aatccaacag ctattttct aacaaccctc tcaagaacca gcaagaaaag gagctggcca       4140
ttaaatgagg ctatcatggc agtcgggatg gtgagcattt tagccagttc tctcctaaaa       4200
aatgatattc ccatgacagg accattagtg gctggagggc tcctcactgt gtgctacgtg       4260
ctcactggac gatcggccga tttggaactg gagagagcag ccgatgtcaa atgggaagac       4320
caggcagaga tatcaggaag cagtccaatc ctgtcaataa caatatcaga agatggtagc       4380
atgtcgataa aaaatgaaga ggaagaacaa acactgacca tactcattag aacaggattg       4440
ctggtgatct caggactttt tcctgtatca ataccaatca cggcagcagc atggtacctg       4500
tgggaagtga agaaacaacg ggccggagta ttgtgggatg ttccttcacc cccacccatg       4560
ggaaaggctg aactggaaga tggagcctat agaattaagc aaaaagggat tcttggatat       4620
tcccagatcg gagccggagt ttacaaagaa ggaacattcc atacaatgtg gcatgtcaca       4680
cgtggcgctg ttctaatgca taaaggaaag aggattgaac caacatgggc ggacgtcaag       4740
aaagacctaa tatcatatgg aggaggctgg aagttagaag gagaatggaa ggaaggagaa       4800
gaagtccagg tattggcact ggagcctgga aaaaatccaa gagccgtcca acgaaaccct       4860 ggtctttca aaaccaacgc cggaacaata ggtgctgtat ctctggactt ttctcctgga       4920
acgtcaggat ctccaattat cgacaaaaaa ggaaaagttg tgggtcttta tggtaatggt       4980
gttgttacaa ggagtggagc atatgtgagt gctatagccc agactgaaaa aagcattgaa       5040
gacaacccag agatcgaaga tcacatttc cgaaagagaa gactgaccat catggaccc       5100 cacccaggag cgggaaagac gaagagatac cttccggcca tagtcagaga agctataaaa       5160
cggggtttga gaacattaat cttggccccc actagagttg tggcagctga atggaggaa       5220 gcccttagag gacttccaat aagataccag acccagcca tcagctgaa gcacaccggg       5280 cgggagattg tggacctaat gtgtcatgcc acatttacca tgaggctgct atcaccagtt       5340
agagtgccaa actacaacct gattatcatg gacgaagcc atttcacaga cccagcaagt       5400
atagcagcta gaggatacat ctcaactcga gtggagatgg gtgaggcagc tgggatttt       5460 atgacagcca ctcccccggg aagcagagac ccatttcctc agagcaatgc accaatcata       5520
gatgaagaaa gagaaatccc tgaacgctcg tggaattccg acatgaatg ggtcacggat       5580 tttaagggga gactgttg gttcgttcca agtataaag caggaaatga tatagcagct       5640
tgcctgagga aaaatggaaa gaaagtgata caactcagta ggaagacctt tgattctgag       5700
tatgtcaaga ctagaaccaa tgattgggac ttcgtggtta caactgacat ttcagaaatg       5760
ggtgccaatt tcaaggctga gagggttata daccccagac gctgcatgaa accagtcata       5820
ctaacagatg gtgaagagcg ggtgattctg gcaggaccta tgccagtgac ccactctagt       5880
gcagcacaaa aagagggag aataggaaga aatccaaaaa atgagaatga ccagtacata       5940
tacatggggg aacctctgga aaatgatgaa gactgtgcac actggaaaga agctaaaatg       6000
ctcctagata acatcaacac gccagaagga atcattccta gcatgttcga accagagcgt       6060
gaaaaggtgg atgccattga tggcgaatac cgcttgagag agaagcaag gaaaaccttt       6120 gtagacttaa tgagaagagg agaccta gtctggttgg cctacagagt ggcagctgaa       6180
ggcatcaact acgcagacag aaggtgtgt tttgatggag tcaagaacaa ccaaatccta       6240
gaagaaaacg tggaagttga atctggaca aaagaagggg aaggagaa attgaaaccc       6300 agatggttgg atgctaggat ctattctgac ccactggcgc taaaagaatt taaggaattt       6360
gcagccggaa gaaagtctct gacccctgaac ctaatcacag aaatgggtag ctcccaacc       6420 ttcatgactc agaaggcaag agacgcactg gacaacttag cagtgctgca cacggctgag       6480
```

```
gcaggtggaa gggcgtacaa ccatgctctc agtgaactgc cggagaccct ggagacattg    6540
cttttactga cacttctggc tacagtcacg ggagggatct ttttattctt gatgagcgca    6600
aggggcatag gaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg gaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtcccta    7020
acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctctttt cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc aaagtttgaa    7320
aagcagttgg gacaagtaat gctcctagtc ctctgcgtga ctcaagtatt gatgatgagg    7380
actacatggg ctctgtgtga ggctttaacc ttagctaccg ggcccatctc cacattgtgg    7440
gaaggaaatc cagggaggtt ttggaacact accattgcgg tgtcaatggc taacattttt    7500
agagggagtt acttggccgg agctggactt ctcttttcta ttatgaagaa cacaaccaac    7560
acaagaaggg gaactggcaa cataggagag acgcttggag agaaatggaa aagccgattg    7620
aacgcattgg gaaaaagtga attccagatc tacaagaaaa gtggaatcca ggaagtggat    7680
agaaccttag caaaagaagg cattaaaaga ggagaaacgg accatcacgc tgtgtcgcga    7740
ggctcagcaa aactgagatg gttcgttgag agaaacatgg tcacaccaga agggaaagta    7800
gtggacctcg gttgtggcag aggaggctgg tcatactatt gtgaggact aaagaatgta    7860 agagaagtca aaggcctaac aaaaggagga ccaggacacg aagaacccat ccccatgtca    7920
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg ccctcagtca tagaaaaaat ggaagcacta    8160
caaaggaaat atggaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
ctcggaagcg gaacccgtaa catcgggatt gaaagtgaga taccaaacct agatataatt    8400
gggaaaagaa tagaaaaaat aaagcaagag catgaaacat catggcacta tgaccaagac    8460
cacccataca aaacgtgggc ataccatggt agctatgaaa caaaacagac tggatcagca    8520
tcatccatgt caacggagt ggtcaggctg ctgacaaaac cttgggacgt tgtcccatg    8580 gtgacacaga tggcaatgac agacacgact ccatttggac aacagcgcgt ttttaaagag    8640
aaagtggaca cgagaaccca gaaccgaaa gaaggcacga gaaactaat gaaaataaca    8700 gcagagtggc tttggaaaga attagggaag aaaaagacac ccaggatgtg caccagagaa    8760
gaattcacaa gaaaggtgag aagcaatgca gccttggggg ccatattcac tgatgagaac    8820
aagtggaagt cggcacgtga ggctgttgaa gatagtaggt tttgggagct ggttgacaag    8880
```

-continued

```
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa aaatcacact agaagaccta aaaaatgaag agatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aaacatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagggga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tct                    10723
```

METHOD OF IMMUNIZATION AGAINST THE 4 DENGUE SEROTYPES

This application claims priority to and incorporates by reference U.S. provisional patent application Ser. No. 60/867,312 filed Nov. 27, 2006, and French patent application number FR 06 08660 filed on Oct. 4, 2006.

The invention relates to a method for inducing a protection against the 4 dengue serotypes in a patient, comprising (a) a first series of administrations (i) of a dose of a vaccinal dengue virus of a first serotype and of a dose of a vaccinal dengue virus of a second serotype, and (ii) of a dose of a vaccinal dengue virus of a third serotype and of a dose of a vaccinal dengue virus of a fourth serotype, and (b) a second series of administrations of doses (i) and (ii), in which the doses (i) and (ii) are administered simultaneously at separate anatomical sites, and in which the second series (b) is implemented at least 30 days to at most 12 months after the first series (a).

Dengue diseases are caused by four viruses of the flavivirus genus, of the serological type, which are similar but distinct from an antigenic point of view (Gübler et al., 1988 In: Epidemiology of arthropod-borne viral disease. Monath T P M, editor, Boca Raton (Fla.): CRC Press: 223-60; Kautner et al., 1997, J. of Pediatrics, 131:516-524; Rigau-Pérez et al., 1998, Lancet; 352: 971-977; Vaughn et al., 1997, J Infect Dis; 176: 322-30). Infection with a dengue serotype can produce a clinical disease spectrum ranging from a nonspecific viral syndrome to a severe hemorrhagic disease which is fatal. The incubation period of dengue fever after a mosquito bite is approximately 4 days (ranging from 3 to 14 days). Dengue fever is characterized by a biphasic fever, headaches, pain in various parts of the body, prostration, eruptions, lymphadenopathy and leukopenia (Kautner et al., 1997, J. of Pediatrics, 131:516-524; Rigau-Pérez et al., 1998, Lancet; 352: 971-977). The viremia period is the same as the febrile period (Vaughn et al., 1997, J. Infect. Dis.; 176: 322-30). Recovery from dengue fever occurs after 7 to 10 days, but there is usually a prolonged asthenia. Decreases in leukocyte and platelet count are common.

Hemorrhagic dengue is a severe febrile disease characterized by anomalies in homeostasis and an increase in vascular permeability which can result in hypovolemia and in hypotension (dengue with shock syndrome) often complicated by severe internal hemorrhaging. The mortality rate of hemorrhagic dengue can be up to 10% without treatment, but is 1% in most centers with experience in treatment (WHO technical Guide, 1986. Dengue haemorrhagic fever: diagnosis, treatment and control, p1-2. World Health Organization, Geneva, Switzerland).

The routine laboratory diagnosis of dengue is based on isolation of the virus and/or detection of antibodies specific for the dengue virus.

Dengue is the second most common tropical infectious disease after malaria, more than half the world's population living in regions where there is a risk of epidemic transmission. Each year, cases of dengue are estimated at 50-100 million, cases of patients hospitalized for hemorrhagic dengue at 500,000, and the number of deaths at 25,000. Dengue is endemic in Asia, in the Pacific region, in Africa, in Latin America and in the Caribbean. More than 100 tropical countries are endemic for dengue virus infections and hemorrhagic dengue has been documented in 60 of these countries (Gubler, 2002, TRENDS in Microbiology. 10:100-103; Monath, 1994, Proc. Natl. Acad. Sci.; 91: 2395-2400). A certain number of well-described factors appear to be involved in dengue: population growth; unplanned and uncontrolled urbanization, in particular in combination with poverty; an increase in air travel; the lack of effective control of mosquitoes and the deterioration of hygiene infrastructures and of public health (Gubler, 2002, TRENDS in Microbiology. 10:100-103). Individuals who travel and expatriates are increasingly warned about dengue (Shirtcliffe et al., 1998, J. Roy. Coll. Phys. Lond.; 32: 235-237). Dengue has constituted one of the main causes of febrile diseases in American troops during deployments in tropical zones endemic for dengue (DeFraites et al., 1994, MMWR 1994; 43: 845-848).

The viruses are maintained in a cycle which involves humans and *Aedes aegypti*, a domestic mosquito which bites during the day, and which prefers to feed off humans. The infection in humans is initiated by injection of the virus while an infected *Aedes aegypti* mosquito feeds on the blood. The virus in the saliva is deposited mainly in the extravascular tissues. The first category of cells infected after inoculation are dendritic cells, which then migrate to the lymph nodes (Wu et al., 2000, Nature Med.; 7:816-820). After an initial replication in the skin and in the lymph nodes, the virus appears in the blood during the acute febrile phase, generally for 3 to 5 days.

Monocytes and macrophages are, with dendritic cells, among the first targets of the dengue virus. Protection against a homotypic reinfection is complete and probably lasts for a lifetime, but crossprotection between the various dengue types lasts less than a few weeks to a few months (Sabin, 1952, Am. J. Trop. Med. Hyg.; 1: 30-50). Consequently, an individual can experience an infection with a different serotype. A second infection with dengue is in theory a risk factor for developing a severe dengue disease. However, hemorrhagic dengue is multifactorial: these factors include the strain of the virus involved, and also the age, the immune status and the genetic predisposition of the patient. Two factors play a major role in the occurrence of hemorrhagic dengue: rapid viral replication with a high viremia (the severity of the disease being associated with the level of viremia; Vaughn et al., 2000, J. Inf. Dis.; 181: 2-9) and a substantially inflammatory response with the release of high levels of inflammatory mediators (Rothman and Ennis, 1999, Virology; 257: 1-6). There is no specific treatment against dengue. The treatment for dengue fever is symptomatic with confinement to bed, control of the fever and of the pain with antipyretics and analgesics, and adequate fluid intake. The treatment for hemorrhagic dengue requires equilibration of fluid losses, replacement of clotting factors and heparin infusion.

Preventive measures are currently based on controlling the vector and taking personal protection steps which are difficult to implement and expensive. No vaccine against dengue has been approved at this time. Given that the four dengue serotypes are in circulation in the world and since they have been reported as being involved in cases of dengue hemorrhagic fever, immunization should ideally confer protection against the four serotypes of the dengue virus.

The use of different anatomical sites for the administration of dengue virus has already been described in the literature.

Thus, Halstead et al. (1973, Am. J. Trop. Med. Hyg., 22:375-381) have shown that an administration of wild-type dengue viruses carried out at 2 or 4 separate anatomical sites for the 4 different serotypes induces protection against a subsequent infection. However, the authors observe no superiority of this type of separate immunization compared with an immunization carried out at a single site.

Attenuated viral forms of dengue viruses result in interferences in humans when they are administered in the form of a tetravalent vaccine. This phenomenon has in particular been described in the following publications: Gubler D. J. Clin. Microbiol. Rev. 1998; 11 (3):480-96; Rothman A. L. et al Vaccine 2001; 19:4694-9.

Zhou H and Deem M W. (Vaccine. 2006 Mar. 24; 24(14): 2451-9) have developed a mathematical model based only on the use of the CD8 epitopes and aimed at simulating the interferences between the CD8 epitopes of the 4 dengue serotypes. According to this theoretical model, the best way of avoiding the interferences would be to carry out a primary immunization using a non-dominant CD8 epitope, followed by a booster by means of an administration at different anatomical sites of the same CD8 epitopes of each of the 4 serotypes.

There exists, therefore, a need for a method for reducing the interferences between the various serotypes and for inducing neutralizing antibodies against the 4 dengue serotypes.

The inventors have demonstrated that it is possible to generate a homologous immune response comprising antibodies that neutralize the 4 serotypes where the latter are administered simultaneously in pairs at separate anatomical sites in a first series of administrations and then in a second series of administrations implemented 30 days to 12 months after the first administration of the 4 serotypes.

The inventors have in particular shown that a DEN-1,2 bivalent immunization concomitant with a DEN-3,4 bivalent immunization, carried out at two separate anatomical sties and followed by a booster of the same vaccinal doses under the same conditions, induces high responses against the four serotypes in all the monkeys immunized with the exception of one serotype in one animal. Conversely, a tetravalent immunization carried out at a single site made it possible to induce a satisfactory response only against two serotypes out of 4.

The immune response generated by the method according to the present invention is therefore quantitatively and qualitatively greater (covers all the serotypes).

According to a first aspect, the present invention relates to a method for inducing a homologous protection against the 4 dengue serotypes in a patient, comprising (a) a first series of administrations (i) of a dose of a vaccinal dengue virus of a first serotype and of a dose of a vaccinal dengue virus of a second serotype, and (ii) of a dose of a vaccinal dengue virus of a third serotype and of a dose of a vaccinal dengue virus of a fourth serotype, and (b) a second series of administrations of doses (i) and (ii), in which the doses (i) and (ii) are administered simultaneously at separate anatomical sites, and in which the second series is implemented at least 30 days and at most 12 months after the first series.

According to another embodiment of the method according to the invention, the vaccinal dengue viruses (i) are administered in the form of a single bivalent vaccinal dose.

According to another embodiment of the method according to the invention, the vaccinal dengue viruses (ii) are administered in the form of a single bivalent vaccinal dose.

According to one specific embodiment of the immunization method according to the invention, said vaccinal dengue virus serotype 1 is selected from the group consisting of the VDV1 strain and of a Chimerivax™ DEN-1.

According to another specific embodiment of the method according to the invention, said vaccinal dengue virus serotype 2 is selected from the group consisting of the VDV2 strain and of a Chimerivax™ DEN-2.

According to another specific embodiment of the method according to the invention, said vaccinal dengue virus serotype 1 is the VDV1 strain and said vaccinal dengue virus serotype 2 is the VDV2 strain.

According to another specific embodiment of the method according to the invention, said vaccinal dengue virus serotype 1 is a Chimerivax™ DEN-1 and said vaccinal dengue virus serotype 2 is a Chimerivax™ DEN-2.

According to another specific embodiment of the method according to the invention, said vaccinal dengue virus serotype 3 is a Chimerivax™ DEN-3.

According to another specific embodiment of the method according to the invention, said vaccinal dengue virus serotype 4 is a Chimerivax™ DEN-4.

According to another specific embodiment of the method according to the invention, the first and second serotypes are, respectively, CYD DEN-1 and CYD DEN-2 and the third and fourth serotypes are, respectively, CYD DEN-3 and CYD DEN-4.

According to another specific embodiment of the method according to the invention, the first and second serotypes are, respectively, CYD DEN-1 and CYD DEN-3 and the third and fourth serotypes are, respectively, CYD DEN-2 and CYD DEN-4.

According to another specific embodiment of the method according to the invention, the amount of vaccinal dengue viruses serotypes 1, 2, 3 and 4 is within a range of from $10^3$ to $10^6$ $CCID_{50}$.

According to another embodiment of the method according to the invention, the vaccinal viruses used in the second series of administrations are identical to those used in the first series of administrations.

According to another embodiment of the method according to the invention, the second series of administrations is implemented 30 to 60 days after the first series of administrations.

An aspect of the present invention is also a kit for immunization against the dengue virus, comprising a container containing at least the vaccinal dengue viruses serotypes 1, 2, 3 and 4

(a) in the form of monovalent compositions containing 4 separate containers, or (b) in the form of two bivalent compositions containing 2 separate containers.

According to one embodiment, the kit according to the invention comprises at least:

(a) a first container containing a bivalent vaccine comprising a Chimerivax™ DEN-1 and a Chimerivax™ DEN-2, and (b) a second container containing a bivalent vaccine comprising a Chimerivax™ DEN-3 and a Chimerivax™ DEN-4.

According to another embodiment, the kit according to the invention comprises at least:

(a) a first container containing a bivalent vaccine comprising a Chimerivax™ DEN-1 and a Chimerivax™ DEN-3, and (b) a second container containing a bivalent vaccine comprising a Chimerivax™ DEN-2 and a Chimerivax™ DEN-4.

An aspect of the present invention is also a kit for immunization against the dengue virus, comprising a container containing at least the vaccinal dengue viruses of a first serotype and of a second serotype, (a) in the form of 2 monovalent compositions contained in 2 separate containers, or (b) in the form of a bivalent composition contained in 1 single container.

According to one embodiment, the kit comprises at least:

(a) a container containing a bivalent vaccine comprising a Chimerivax™ DEN-1 and a Chimerivax™ DEN-3, or (b) a container containing a bivalent vaccine comprising a Chimerivax™ DEN-2 and a Chimerivax™ DEN-4, or (c) a container containing a bivalent vaccine comprising a Chimerivax™ DEN-1 and a Chimerivax™ DEN-2, or (d) a container containing a bivalent vaccine comprising a Chimerivax™ DEN-3 and a Chimerivax™ DEN-4.

The present invention also provides a bivalent composition or a bivalent vaccine comprising an immunoeffective amount of the dengue vaccinal viruses of a first serotype and of a second serotype and a pharmaceutically acceptable excipient.

According to a specific embodiment, the bivalent composition or vaccine comprises the vaccinal viruses selected from the group consisting of: Chimerivax™ DEN-1 and Chimerivax™ DEN-3; or Chimerivax™ DEN-2 and Chimerivax™ DEN-4; or Chimerivax™ DEN-1 and a Chimerivax™ DEN-2; or Chimerivax™ DEN-3 and Chimerivax™ DEN-4.

The invention will be described in further detail in the description which follows.

Definitions

In the context of the present invention, two anatomical sites are "separate" if they are drained by different lymph nodes. For example, the right arm and the left arm are considered to be separate sites. The following separate sites are non-limiting examples: right arm/right thigh; left arm/left thigh, left arm/right thigh.

In the context of the present invention, the term "simultaneous administrations" is intended to mean administrations implemented on the same day (i.e. at most 24 h). Simultaneous administrations are advantageously carried out at most 1 hour apart, conventionally 1-5 minutes apart.

In the context of the present invention, the doses (i) are administered at a first anatomical site, either in the form of two monovalent doses or in the form of a single bivalent dose. The doses (ii) are, for their part, administered simultaneously at a second anatomical site, either in the form of two monovalent doses or in the form of a single bivalent dose, the first and second sites being separate sites as defined above.

"Dengue viruses" or "DENs" are positive, single-stranded RNA viruses belonging to the *Flavivirus* genus of the flaviviridae family. The genomic RNA contains a type I cap at the 5' end but lacks a poly-A tail at the 3' end. The genomic organization consists of the following elements: 5' noncoding region (NCR), structural proteins (capsid (C), premembrane/membrane (prM/M), envelope (E)) and nonstructural proteins (NS1-NS2A-NS2B-NS3-NS4A-NS4B-NS5), and 3' NCR. The genomic viral RNA is associated with the capsid proteins so as to form a nucleocapsid. As for the other flaviviruses, the DEN viral genome encodes an uninterrupted coding region which is translated into a single polyprotein.

In the context of the present invention, the term "vaccinal dengue virus" is intended to mean any viral form of the dengue virus capable of inducing a specific homologous immune response, preferably any viral form of the dengue virus that can be used in the context of an immunization program in humans against dengue virus infection. The term "vaccinal dengue viruses" is therefore intended to mean inactivated viruses, attenuated viruses, or recombinant proteins such as the dengue virus envelope protein.

A vaccinal virus is considered to be "inactivated" if it no longer replicates on permissive cells.

A vaccinal virus is considered to be "attenuated" if, after growth at 37° C. or 39° C. on Huh-7, VERO and/or C6/36 hepatic cells, said vaccinal virus has a maximum titer that is at least 10-fold less than the maximum titer obtained with the wild-type parental strain under the same culture conditions and as measured using the tittering method. A vaccinal virus that exhibits decreased growth on at least one of the three cell types identified above is therefore considered to be "attenuated" in the context of the present invention.

A vaccinal virus that can be used in humans has a positive benefit/risk ratio, said ratio generally making it possible to comply with the regulatory requirements for obtaining a marketing authorization. A vaccinal dengue virus used in the context of the present invention is preferably an attenuated virus such that it does not induce the disease in humans. Advantageously, said vaccinal virus produces only side effects that are at most of moderate intensity (i.e., moderate to weak, or even zero) in the majority of the individuals immunized, while at the same time conserving its ability to induce a neutralizing antibody response.

By way of nonlimiting examples of vaccinal dengue virus that can be used in the context of the present invention, mention may be made of: inactivated vaccinal viruses, attenuated vaccinal viruses such as the attenuated strains VDV-1 or VDV-2, the strains described, for example, in applications: WO02/66621, WO0057904, WO0057908, WO0057909; WO0057910, WO02/0950075 and WO02/102828, or chimeras. Chimeric viruses have the particularity of having the characteristics of the attenuated viruses as defined above. Any chimeric virus expressing the dengue virus envelope protein and inducing an immune response comprising antibodies that neutralize the serotype from which the envelope protein is derived can therefore be used in the context of the present invention. By way of nonlimiting examples, mention may be made of: the dengue Chimerivax™ products as described, for example, in patent application WO 98/37911, and the dengue/dengue chimeras as described, for example, in patent applications WO 9640933 and WO0160847. The vaccinal dengue virus serotype 1 may, for example, be the VDV1 vaccinal strain or a Chimerivax™ DEN-1, in particular a YF17D/DEN-1 virus, or else a 16007/PDK13 DEN-1 strain. The vaccinal dengue virus serotype 2 may, for example, be the VDV2 vaccinal strain or a Chimerivax™ DEN-2, in particular a YF17D/DEN-2 virus, or else a 16681/PDK53 DEN-2 strain. The vaccinal dengue virus serotype 3 may be a Chimerivax™ DEN-3, in particular a YF17D/DEN-3 virus. The vaccinal dengue virus serotype 4 may be a Chimerivax™ DEN-4, in particular a YF17D/DEN-4 virus. This strain was described in patent application EP1159968 in the name of Mahidol University and was deposited with the Collection Nationale de Cultures de Microorganismes (CNCM) [National Collection of Microorganism Cultures] under the number I-2483.

"VDV" or "Vero dengue vaccine" denotes a live attenuated dengue viral strain adapted on Vero cells and capable of inducing a specific humoral response, including the induction of neutralizing antibodies, in primates and in particular in humans.

"VDV-1" is a strain obtained from a wild-type strain DEN-1 16007 which was subjected to 11 passages on PDK cells (DEN-1 16007/PDK11), which was then amplified on Vero cells at 32° C., and the RNA of which was purified and transfected into Vero cells. The VDV-1 strain has 14 additional mutations compared to the vaccinal strain DEN-1 16007/PDK13 (13 passages on PDK—Primary Dog Kidney—cells). The DEN-1 16007/PDK13 strain, also called "LAV1", was described in patent application EP1159968 in the name of Mahidol University and was deposited with the Collection Nationale de Cultures de Microorganismes (CNCM) under the number 1-2480. The complete sequence of the VDV-1 strain is given in the sequence SEQ ID NO:1. Said strain can be readily reproduced from said sequence. A method of preparation and the characterization of the VDV-1 strain have been described in the International patent application filed under the names of Sanofi-Pasteur and of the Center for Disease Control and Prevention under the number PCT/IB 2006/001313.

"VDV-2" is a strain obtained from a wild-type strain DEN-2 16681 which was subjected to 50 passages on PDK cells (DEN-2 16681/PDK50), and plaque-purified, and the RNA of which was extracted and purified before being transfected into Vero cells. The VDV-2 strain was then obtained by plaque-purification and amplification on Vero cells. The VDV-2 strain has 10 additional mutations compared with the vaccinal strain DEN-2 16681/PDK53 (53 passages on PDK cells), 4 mutations of which are silent. The DEN-2 16681/PDK53 strain, also called "LAV2", was described in patent application EP1159968 in the name of Mahidol University and was deposited with the Collection Nationale de Cultures de Microorganismes (CNCM) under the number I-2481. The complete sequence of the VDV-2 strain is shown in the sequence SEQ ID NO:2. The VDV-2 strain can be readily reproduced from said sequence. A method of preparation and of characterization of the VDV-2 strain has been described in the International patent application filed in the names of Sanofi-Pasteur and of the Center for Disease Control and Prevention under the number PCT/IB 2006/001513.

The VDV 1 and 2 strains are prepared by amplification on Vero cells. The viruses produced are harvested and clarified with respect to cell debris by filtration. The DNA is digested by enzymatic treatment. The impurities are removed by ultrafiltration. The infectious titers can be increased by means of a method of concentration. After the addition of a stabilizer, the strains are stored in lyophilized or frozen form before use, and then reconstituted extemporaneously.

The term "ChimeriVax™ dengue" or "CYD" denotes a chimeric yellow fever (YF) virus which comprises the backbone of a YF virus in which the sequences encoding the premembrane and envelope proteins have been replaced with those of a DEN virus. The term "CYD-1 or CYD DEN1" is thus used to describe a chimeric YF virus containing the prM and E sequences of a dengue serotype 1 strain (DEN-1). The term "CYD-2 or CYD DEN2" is used to describe a chimeric YF virus containing the prM and E sequences of a DEN-2 strain. The term "CYD-3 or CYD DEN3" is used to describe a chimeric YF virus containing the prM and E sequences of a DEN-3 strain. The term "CYD-4 or CYD DEN4" is used to describe a chimeric YF virus containing the prM and E sequences of a DEN-4 strain. The preparation of these ChimeriVax™ dengues has been described in detail in International patent applications WO 98/37911 and WO 03/101397, to which reference may be made for a precise description of the method for preparing them. The chimeras described in the examples were generated using the prM and E sequences derived from the DEN1 PUO359 (TYP1140), DEN2 PU0218, DEN3 PaH881/88 and DEN4 1288 (TVP 980) strains. Any strain of the dengue virus could be used in the context of the present invention for the construction of the chimeras.

Preferably, the chimeric YF virus comprises the backbone of an attenuated yellow fever strain YF17D (Theiler M, and Smith H H (1937) J. Exp. Med. 65, p767-786.) (YF17D/DEN-1, YF17D/DEN-2, YF17D/DEN-3, YF17D/DEN-4 virus). Examples of YF17D strains which can be used include YF17D204 (YF-Vax®, Sanofi-Pasteur, Swifwater, Pa., USA; Stamaril®, Sanofi-Pasteur, Marcy I'Etoile, France; ARIL-VAX™, Chiron, Speke, Liverpool, UK; FLAVIMUN®, Berna Biotech, Bern, Switzerland); YF17D-204 France (X15067,X15062); YF17D-204,234 US (Rice et al., 1985, Science, 229:726-733), or else related strains YF17DD (Genbank accession number U17066), YF17D-213 (Genbank accession number U17067) and the YF17DD strains described by Galler et al. (1998, Vaccines 16(9/10):1024-1028). Any other yellow fever virus strain attenuated for use in humans can be used in the context of the present invention for the construction of the chimeras.

An aspect of the present invention is therefore also a bivalent composition or vaccine comprising an immunoeffective amount of a vaccinal dengue virus of a first serotype and of a vaccinal dengue virus of a second serotype and a pharmaceutically acceptable excipient.

For a description of the vaccinal viruses that can be used in the vaccines according to the invention, reference may be made to the description given thereof in the context of the method of immunization according to the invention.

According to a specific embodiment, the bivalent composition or vaccine according to the invention comprises CYD DEN-1 and CYD DEN-2, or CYD DEN-3 and CYD DEN-4, or CYD DEN-1 and CYD DEN-3 or CYD DEN-2 and CYD DEN-4; advantageously, the vaccinal viruses are present in the vaccine in an amount of $10^5$ $CCID_{50}$.

Each ChimeriVax™ monovalent vaccinal dengue virus (serotypes 1, 2, 3 and 4) was prepared by amplification of each serotype on Vero cells. More specifically, the four viruses are produced separately on adherent Vero cells in serum-free medium. The viral harvest, clarified with respect to cell debris by filtration, is then concentrated and purified by ultrafiltration and chromatography in order to remove the host cell DNA. After the addition of a stabilizer, the vaccinal strains are stored in frozen or lyophilized form before use, and are then reconstituted extemporaneously. The same method is applied for the four chimeras.

A dose, a composition or a vaccine is "monovalent" when it contains, in addition to a pharmaceutically acceptable excipient, a single dengue virus serotype. A dose, a composition or a vaccine is "bivalent" when it contains two different dengue virus serotypes. A dose, a composition or a vaccine is "trivalent" when it contains three different dengue virus serotypes. A dose, a composition or a vaccine is "tetravalent" when it contains four different dengue virus serotypes. The multivalent compositions are obtained by simply mixing the monovalent compositions.

The term "patient" denotes an individual (child or adult) who may be infected with dengue, in particular an individual at risk of infection, such as, for example, an individual who travels in regions where dengue is present or an inhabitant of these regions. This term therefore encompasses individuals who are naive and also individuals who are non-naive with respect to the dengue virus.

Sequential Immunization at Separate Anatomical Sites

The inventors have shown in particular that the administration of the 4 serotypes in the form of two simultaneous bivalent administrations at separate anatomical sites, followed by a booster 30 days to 12 months after the first series of administrations, makes it possible to obtain an effective homologous protection against the 4 serotypes. The method according to the present invention is therefore most particularly valuable in the context of an immunization strategy against dengue.

According to the present invention, the 4 dengue serotypes can be administered in any order provided that they are administered in pairs (i.e. doses (i) and (ii), respectively, in the form of two monovalent doses or of a single bivalent dose) simultaneously at separate sites.

The method according to the present invention can therefore be implemented with the embodiments described below:
(i) serotypes 1 and 2; (ii) serotypes 3 and 4; or
(i) serotypes 1 and 3; (ii) serotypes 2 and 4; or
(i) serotypes 1 and 4; (ii) serotypes 2 and 3; or
(i) serotypes 2 and 3; (ii) serotypes 1 and 4; or
(i) serotypes 2 and 4; (ii) serotypes 1 and 3; or
(i) serotypes 3 and 4; (ii) serotypes 1 and 2.

Preferably, the method according to the present invention comprises the administration of the following vaccinal dengue viruses: (i) serotypes 1 and 2; (ii) serotypes 3 and 4 or (i) serotypes 1 and 3; (ii) serotypes 2 and 4. The doses (i) and (ii) are advantageously in the form of bivalent doses.

According to specific embodiments the present invention therefore covers the following schemes:
(i) CYD DEN-1 and CYD DEN-2; (ii) CYD DEN-3 and CYD DEN-4
(i) CYD DEN-1 and CYD DEN-3; (ii) CYD DEN-2 and CYD DEN-4
(i) CYD DEN-1 and CYD DEN-4; (ii) CYD DEN-2 and CYD DEN-3
(i) CYD DEN-2 and CYD DEN-3; (ii) CYD DEN-1 and CYD DEN-4
(i) CYD DEN-2 and CYD DEN-4; (ii) CYD DEN-1 and CYD DEN-3
(i) CYD DEN-3 and CYD DEN-4; (ii) CYD DEN-1 and CYD DEN-2
(i) VDV-1 and CYD DEN-2; (ii) CYD DEN-3 and CYD DEN-4
(i) VDV-1 and CYD DEN-3; (ii) CYD DEN-2 and CYD DEN-4
(i) VDV-1 and CYD DEN-4; (ii) CYD DEN-2 and CYD DEN-3
(i) CYD DEN-2 and CYD DEN-3; (ii) VDV-1 and CYD DEN-4
(i) CYD DEN-2 and CYD DEN-4; (ii) VDV-1 and CYD DEN-3
(i) CYD DEN-3 and CYD DEN-4; (ii) VDV-1 and CYD DEN-2
(i) CYD DEN-1 and VDV-2; (ii) CYD DEN-3 and CYD DEN-4
(i) CYD DEN-1 and CYD DEN-3; (ii) VDV-2 and CYD DEN-4
(i) CYD DEN-1 and CYD DEN-4; (ii) VDV-2 and CYD DEN-3
(i) VDV-2 and CYD DEN-3; (ii) CYD DEN-1 and CYD DEN-4
(i) VDV-2 and CYD DEN-4; (ii) CYD DEN-1 and CYD DEN-3
(i) CYD DEN-3 and CYD DEN-4; (ii) CYD DEN-1 and VDV-2
(i) VDV-1 and VDV-2; (ii) CYD DEN-3 and CYD DEN-4
(i) VDV-1 and CYD DEN-3; (ii) VDV-2 and CYD DEN-4
(i) VDV-1 and CYD DEN-4; (ii) VDV-2 and CYD DEN-3
(i) VDV-2 and CYD DEN-3; (ii) VDV-1 and CYD DEN-4
(i) VDV-2 and CYD DEN-4; (ii) VDV-1 and CYD DEN-3 and
(i) CYD DEN-3 and CYD DEN-4; (ii) VDV-1 and VDV-2.

Preferably, the method of immunization according to the invention comprises the administration of the following vaccinal dengue viruses: (i) CYD DEN-1 and CYD DEN 2; (ii) CYD DEN-3 and CYD DEN-4; or (i) CYD DEN-1 and CYD DEN-3; (ii) CYD DEN-2 and CYD DEN-4. The doses (i) and (ii) are advantageously in the form of bivalent doses.

The method of immunization according to the present invention comprises a second series of administrations implemented from 30 days to 12 months, advantageously from 30 days to 3 months, preferably 30 days, 45 days or 60 days, after the first series of administrations (i and ii), which advantageously comprises the administration of the same compositions as those used in the first series, which are advantageously administered under the same conditions.

In the context of the present invention, the term "dose of vaccinal virus" is intended to mean a composition comprising an "immunoeffective amount" of the vaccinal dengue virus, i.e. an amount of dengue virus sufficient to induce a homologous neutralizing antibody response, which can be demonstrated, for example, by means of the seroneutralization test as described below in example 1. A serum is considered to be positive for the presence of neutralizing antibodies when the neutralizing antibody titer thus determined is greater than or equal to 1:10 (unit: 1/dilution).

Vaccinal strain amounts are commonly expressed in terms of viral plaque-forming units (PFU) or of 50% tissue culture infectious dose, or else of 50% cell culture infectious dose ($CCID_{50}$). For example, the compositions according to the invention can contain from 10 to $10^6$ $CCID_{50}$, in particular from $10^3$ to $10^5$ $CCID_{50}$ of vaccinal dengue virus serotype 1, 2, 3 or 4 for a monovalent or bivalent composition. Thus, in the compositions or use according to the invention, the doses of vaccinal dengue viruses serotypes 1, 2, 3 and 4 are preferably each within a range of from 10 to $10^6$ $CCID_{50}$, such as 10, $10^1$, $10^2$, $10^3$, $10^4$, $10^5$ or $10^6$ $CCID_{50}$, in particular in a range from $10^3$ to $10^5$ $CCID_{50}$. The vaccinal viruses can be used at identical or different doses, which can be adjusted according to the nature of the vaccinal virus used and to the strength of the immune response obtained.

According to a specific embodiment of the method according to the present invention, the monovalent or bivalent doses of vaccinal viruses comprise, respectively, $10^5$ $CCID_{50}$ of CYD DEN-1, of CYD DEN-2, of CYD DEN-3 and of CYD DEN-4.

The neutralizing antibody response is advantageously a lasting response, i.e. it can be detected in the serum at least 6 months after the second series of administrations (i) and (ii).

The dose of a vaccinal dengue virus of a first serotype and the dose of a vaccinal dengue virus of a second serotype (i.e. dose(s) (i)) are administered simultaneously in the form of two monovalent compositions, or advantageously in the form of a single bivalent composition or dose.

Similarly, the dose of a vaccinal dengue virus of a third serotype and the dose of a vaccinal dengue virus of a fourth serotype (i.e. dose(s) (ii)) are administered simultaneously in the form of two monovalent vaccinal compositions, or advantageously in the form of a single bivalent vaccinal composition.

The vaccinal viruses are administered in the form of vaccinal compositions or vaccinal virus doses which can be prepared according to any method known to those skilled in the art. Usually, the viruses, generally in lyophilized form, are mixed with a pharmaceutically acceptable excipient, such as water or a phosphate buffered saline solution, wetting agents or stabilizers. The term "pharmaceutically acceptable excipient" is intended to mean any solvent, dispersing medium, filler, etc., which does not produce a side reaction, for example an allergic reaction, in humans or animals. The excipient is selected according to the pharmaceutical form chosen, and to the method and route of administration. Appropriate excipients and also the requirements in terms of pharmaceutical formulation are described in "Remington: The Science & Practice of Pharmacy", for example, which represents a reference work in the field.

Preferably, the vaccinal compositions are prepared in an injectable form, and can be liquid solutions, suspensions or emulsions. The compositions can include, in particular include an aqueous solution buffered so as to maintain a pH of between approximately 6 and 9 (as determined with a pH meter at ambient temperature).

Although it is not necessary to add an adjuvant, the compositions can nevertheless include such a compound, i.e. a substance which increases, stimulates or strengthens the cellular or humoral immune response induced by the vaccinal strain administered simultaneously. It is a routine matter for those skilled in the art to select, from the adjuvants conventionally used in the field of vaccines, an adjuvant which may be suitable in the context of the present invention.

The vaccinal compositions according to the invention can be administered according to any route normally used in immunization, for example parenterally (in particular intradermally, subcutaneously or intramuscularly), advantageously subcutaneously. Preferably, the vaccinal compositions are injectable compositions administered subcutaneously in the left deltoid and the right deltoid region.

The volume of composition administered depends on the route of administration. For subcutaneous injections, the volume is generally between 0.1 and 1.0 ml, preferably approximately 0.5 ml.

The optimal period for the administration of all the serotypes 1 to 4, is approximately 1 to 3 months before exposure to the dengue virus. The vaccines can be administered as a prophylactic treatment for infection with a dengue virus in adults and children. Target populations therefore include individuals who may be naive (i.e. not previously immunized) or non-naive with respect to the dengue virus.

Vaccinal dengue virus serotypes 1 to 4 booster administrations can also be carried out, for example, between 6 months and 10 years, for example 6 months, 1 year, 3 years, 5 years or 10 years, after administration of the second series of administrations according to the invention. The booster administrations will advantageously be implemented using the same vaccinal compositions (i.e. the same vaccinal viruses) and preferably under the same administration conditions (anatomical sites and routes of administration) as those used for the 1st and 2nd series of administrations.

The interference phenomena can be explained by the dominance of one or more serotypes compared with others, and are therefore independent of the technology used to manufacture the vaccine candidate (for example, VDV or chimerivax). The method according to the present invention can therefore apply in general to any vaccinal dengue virus.

An aspect of the present invention is therefore also the use of doses of vaccinal dengue virus for the preparation of a vaccine for inducing a protection against the 4 dengue serotypes, comprising:

(a) a first series of administrations (i) of a dose of a vaccinal dengue virus of a first serotype and of a dose of a vaccinal dengue virus of a second serotype, and (ii) of a dose of a vaccinal dengue virus of a third serotype and of a dose of a vaccinal dengue virus of a fourth serotype, and (b) a second series of administrations of doses (i) and (ii), in which the doses (i) and (ii) are administered simultaneously at separate anatomical sites, and in which the second series is implemented at least 30 days to at most 12 months after the first series.

For a description of the vaccinal dengue viruses that can be used in the context of the present invention, reference may be made to the description given thereof in relation to the method of immunization according to the invention.

An aspect of the present invention is also a kit for immunization against the four dengue virus serotypes. The kit according to the present invention comprises the doses as defined above in relation to the method of immunization proposed. The kit according to the invention therefore comprises a container containing the various containers containing the vaccinal doses and, optionally, an instruction leaflet containing the information useful for administration of the vaccines.

According to one embodiment, the kit according to the invention comprises a container containing at least the vaccinal dengue viruses serotypes 1, 2, 3 and 4

(a) in the form of monovalent compositions contained in 4 separate containers, or (b) in the form of two bivalent compositions contained in 2 separate containers.

According to another embodiment, the kit according to the invention comprises a container containing at least the vaccinal dengue viruses of a first serotype and of a second serotype, (a) in the form of two monovalent compositions contained in 2 separate containers, or (b) in the form of a bivalent composition contained in 1 single container.

For a description of the vaccinal dengue viruses that can be used in the kit according to the invention, reference may be made to the description of the vaccinal viruses given above in relation to the method of immunization according to the invention.

According to a specific embodiment, the kit according to the present invention therefore comprises at least:

(a) a first container containing a bivalent vaccine comprising a Chimerivax™ DEN-1 and a Chimerivax™ DEN-2, and (b) a second container containing a bivalent vaccine comprising a Chimerivax™ DEN-3 and a Chimerivax™ DEN-4.

According to another embodiment, the kit according to the invention comprises at least:

(a) a first container containing a bivalent vaccine comprising a Chimerivax™ DEN-1 and a Chimerivax™ DEN-3, and (b) a second container containing a bivalent vaccine comprising a Chimerivax™ DEN-2 and a Chimerivax™ DEN-4.

According to another embodiment, the kit according to the invention comprises at least:

(a) a container containing a bivalent vaccine comprising a Chimerivax™ DEN-1 and a Chimerivax™ DEN-3, or (b) a container containing a bivalent vaccine comprising a Chimerivax™ DEN-2 and a Chimerivax™ DEN-4, or (c) a container containing a bivalent vaccine comprising a Chimerivax™ DEN-1 and a Chimerivax™ DEN-2, or (d) a container containing a bivalent vaccine comprising a Chimerivax™ DEN-3 and a Chimerivax™ DEN-4.

The kits according to the invention may contain a single example or several examples of the containers as described above.

If the vaccines used are in lyophilized form, the kit will advantageously comprise at least one additional container containing the diluent for reconstituting an injectable vaccinal dose. Any pharmaceutically acceptable diluent may be used to do this, conventionally water or a phosphate buffered aqueous solution.

The invention is illustrated by means of the following examples.

EXAMPLES

Example 1

Immunization in Monkeys by Simultaneous Injection of Two Bivalent Compositions at Separate Anatomical Sites The viremia and the immunogenicity were tested in a monkey model. The viremia, in particular, was identified as one of the factors associated with the virulence and the severity of the disease in man and therefore constitutes an important parameter to be taken into consideration. The immunogenicity is, for its part, a key parameter in the context of the evaluation of the protection conferred.

1.1 Materials and Methods:

The experiments in monkeys were carried out according to the European Directives relating to animal experimentation. The immunizations were carried out in cynomolgus monkeys (*Macaca fascicularis*) originating from Mauritania. The monkeys were placed in quarantine for six weeks before immunization.

The monkeys were immunized subcutaneously in the arms with 0.5 ml of vaccinal composition. After a light anesthesia with ketamine (Imalgene, Merial), blood was collected by puncture from the inguinal or saphenous veins. At day 0 and 28 following each immunization, 5 ml of blood were sampled in order to evaluate the antibody responses, while, between days 2 and 10, 1 ml of blood was sampled in order to evaluate the viremia. The blood was collected on ice and stored on ice until serum separation. To do this, the blood was centrifuged for 20 minutes at 4° C. and the serum collected was stored at −80° C. until the time of the tests.

Measurement of Viremia

The post-vaccinal viremias were monitored by quantitative real-time RP-PCR (qRT-PCR). Two sets of primers and of probes located in the NS5 gene of the DEN1 and DEN2 strains were used to quantify the VDV-1 RNA and VDV-2 RNA, respectively. A third set of 2 primers and of 1 probe located in the NS5 gene of the YF virus was used to quantify the CYD RNA. Finally, 4 sets of primers and of probes specific for the various CYD serotypes, located at the junction of the E (DEN)/NS1 (YF) genes were used to identify the serotype in the samples positive for the YF NS5 RNA (see also table I). 7 plasmids containing, under the control of the T7 promoter, the region targeted by each PCR were transcribed in vitro so as to generate a series of synthetic RNAs which were included as an internal reference in each RT-PCR assay. These synthetic RNAs were assayed by spectrophotometry, and the amount of RNA obtained was converted to number of RNA copies and expressed as GEQ (genomic equivalents).

0.140 ml of monkey serum was extracted using the Macherey Nagel "Nucleospin 96 virus™" RNA extraction kit, according to the manufacturer's instructions, and then the purified RNA was eluted with 0.140 ml (0.090 ml, then 0.05 ml) of RNase-free water. In order to avoid repeated freezing/thawing cycles, a first quantification was carried out immediately after the extraction, on 5 μl of said RNA preparation. The remaining volume was frozen at 70° C.

The reaction mixtures contained, in addition to the components of the "Qiagen Qauntitect™ probes" RT-PCR quantification kit (Qiagen), 10 picomol of each primers, 4 picomol of each probe and 5 μl of RNA, in the total volume of 25 μl. In the case of the RNAs to be tested, 5 μl of the purified preparation were directly introduced into the reaction mixture, without any prior dilution step. The synthetic RNAs were diluted to 1/10 in RNAse-free water, and 7 dilutions containing approximately 10 to $10^6$ GEQ in 5 μl were quantified in parallel in order to generate the standard curve.

The quantification reactions were carried out on the Applied Biosystem ABIPrism 700™ device, using the following program: 50° C./30 min, 95° C./15 min, then 40 cycles of 95° C./15 sec-60° C./60 sec.

The limit of quantification of the viral RNA in this test is from 2.9 to 3.3 $\log_{10}$GEQ/ml (800 to 2000 GEQ/ml; 4 to 10 GEQ/reaction), according to the PCR targets (standard deviation: +/−0.3 $\log_{10}$).

The correlation between the infectious titer and the viral RNA quantification was established in parallel to the assays, by analysis of 0.140 ml of negative monkey serum samples (DO) to which a known amount of infectious particles of the viruses which were used for the immunization (CYD or VDV) were added. Said control sera were prepared at two dilutions containing approximately 1 PFU and approximately 100 PFU in 5 μl (2.3 and 4.3 $\log_{10}$ PFU/ml, respectively).

In the tests used in the examples, the correlation between GEQ and PFU is the following:GEQ/PFU ratio of 2.7 $\log_{10}$ (i.e.: 1 PFU=500 GEQ) for the sera positive for YF or CYDs. GEQ/PFU ratio of 2.5 $\log_{10}$ (i.e.: 1 PFU=320 GEQ) for the sera positive for VDV1 or VDV2.

The quantification limits being <3.3 $\log_{10}$GEQ/ml (i.e.: <4 PFU/ml) for qRT-PCR YF and CYDs and <2.9 $\log_{10}$GEQ/ml (i.e.: <2.5 PFU/ml) for qRT-PCR VDV1 and VDV2.

The primers and probes used are given in table 1 below, in which are listed, in order, for each assay, the sense and antisense primers and the probe.

TABLE 1

| | | | sequence |
|---|---|---|---|
| Y | YF-NS5 | sense | 5' GCACGGATGTAACAGACTGAAGA (23 bases) |
| F | YF NS5 | anti | 5' CCAGGCCGAACCTGTCAT (18 bases) |
| | YF-NS5 | | 5' Fam- CGACTGTGTGGTCCGGCCCATC-Tamra (22 bases) |
| CYD1 | CYD1- | sense | 5' CATTGC AGT TGG CCT GGT AA (20 b) |
| spe | CYD1- | anti | 5' CTT TGG CAA GAG AGA GCT CAA GT (23 b) |
| | CYD1- | | 5' Fam-CCG ATC AAG GAT GCG CCA TCA-Tamra (21 b) |
| CYD2 | CYD2- | sense | 5' GTG GGA GTC GTG ACG CTG TA (20 b) |
| spe | CYD2- | anti | 5' GTT GAT GGC GCA TCC TTG ATC (21 b) |
| | CYD2- | | 5' Fam-TGG GAG TTA TGG TGG GCG CCG-Tamra (21 b) |
| CYD3 | CYD3- | sense | 5' AAA ACA CTT CCA TGT CAT TTT CAT G (25 b) |
| spe | CYD3- | anti | 5' GTT GAT GGC GCA TCC TTG ATC (21 b) |
| | CYD3- | | 5' Fam-TGCGATAGGAATTATCACACTCTATCTGGGAGC-Tamra (33 b) |

TABLE 1-continued

```
                  sequence
CYD4  CYD4-    sense  5' CTT AGT ATT GTG GAT TGG CAC GAA (24 b)
spe   CYD4-    anti   5' GCG CCA ACT GTG AAA CCT AGA (21 b)
      CYD4-           5' -Fam-AGAAACACTTCAATGGCAATGACGTGCAT-Tamra (29 b)

VDV1  VDV1-NS5 sense  5' TCG CAA CAG CCT TAA CAG C (19 b)
spe   VDV1-NS5 anti   5' ACT ATC TCC CTC CCA TCC TTC (21 b)
      VDV1-NS5        5' Fam-TTC ACA CCA CTT CCA C-M GB/NFQ (16 b)

VDV2  VDV2-NS5 sense  5' AAT GAC AGA CAC GAC TCC (18 b)
spec  VDV2-NS5 anti   5' CCC AAA ACC TAC TAT CTT CAA C (22 b)
      VDV2-NS5        5' Fam-TGG AAG TCG GCA CGT GA-MGB/NFQ (17 b)
```

Measurement of Neutralizing Antibodies (Seroneutralization Test) (SN50)

Conventionally, the dengue antibody measurement is established using the PRNT50 (50% PFU number reduction neutralization test). Since this test is laborious and uses up a lot of material, we developed the SN50 test, based on 50% reduction in the number of units measured in a CClD50 test.

In a 96-well plate, 0.120 ml of each decomplemented serum is added to 0.480 ml of diluent (ISCOVE 4% FCS) per well. 6-fold serial dilutions are prepared by transfer of 0.150 ml of serum into 0.450 ml of diluent. 450 μl of virtual dilution at $2.7 \log_{10}$ CCID50/ml are added to each well so as to obtain 25 CCID50/well. The plate is incubated at 37° C. for 1 hour. 0.1 ml of each dilution is then distributed into 6 wells of a 96-well plate into which VERO cells had been seeded 3 days before the beginning of the experiment at a density of 8000 cells/well, in 0.1 ml of ISCOVE medium containing 4% FCS. After incubation at 37° C. for 6 days, in the presence of 5% $CO_2$, the cells are fixed with an ethanol/acetone (70/30) mixture at 4° C. for 15 minutes, and then washed 3 times in PBS and incubated for 1 h at 37° C. in the presence of 0.05 ml of a 1/2000 dilution of an anti-flavivirus monoclonal antibody (mAb 4G2). The plates are then washed twice and incubated for 1 h at 37° C. in the presence of 0.05 ml of a 1/1000 dilution of an alkaline phosphatase-conjugated anti-mouse IgG. The lysis plaques are visualized by adding 0.05 ml of a colored substrate: BCIP/NBT. The neutralizing antibody titers are calculated using the Karber formula as defined below:

$$\log_{10} SN50 = d + f/N(X + N/2),$$

in which:
d represents the dilution resulting in 100% neutralization (i.e. 6 negative replicates, i.e. replicates exhibiting no sign of infection)
f: represents the dilution factor in log 10 (e.g. dilution factor of 1:4, f=0.6)
N: represents the number of replicates/dilution (N=6)
X: total number of wells exhibiting no sign of infection, with the exception of the dilution d The limit of viral detection is 10 SN50 (i.e. $1.0 \log_{10}$ SN50).

The viral strains which were used for the neutralization are the DEN1 16007, DEN2 16681, DEN3 16562 or DEN4 1036 strains. For the controls, the initial viral dilutions were re-titrated.

The correlation between the neutralizing titer measured in the SN50 test and the neutralizing titer measured conventionally in the PRNT50 test is: $\log_{10} PRNT50 = \log_{10} SN50 + 0.2$ The mean titer (GMT) is established by calculating the geometric mean of the titers expressed in linear value; the samples for which the titer is less than the detection threshold are, by convention, assigned a value equal to half this threshold.

1.2 Evaluation of the Sequential Immunizations 2 groups of 4 monkeys of equivalent age and weight were immunized (see table 2).

The immunization was carried out subcutaneously in the arm, with a 23G1 needle, at a dose of $10^5$ $CCID_{50}$ for each serotype for the CYD DEN 1 to 4 vaccines.

TABLE 2

Composition of the groups and immunization protocol Monkeys

| | | Immunizations | |
|---|---|---|---|
| Group | D0 | | D58 |
| 1 | CYD-1,2 in one arm<br>CYD-3,4 in the other arm | | CYD-1,2 in one arm<br>CYD-3,4 in the other arm |
| 2 | CYD-1,2,3,4 | | CYD-1,2,3,4 |

The immunogenicity results obtained after one immunization (D28) and two immunizations (D86) are given in table 3.

The viremia results are given in table 4.

TABLE 3

SN50 neutralizing titer (units 1/dil)

| | | Monkeys | | | | | | | | |
|---|---|---|---|---|---|---|---|---|---|---|
| | | Immunizations | | D + 28 | | | | D58 + 28 | | | |
| Group | ID | D0 | D58 | DEN-1 | DEN-2 | DEN-3 | DEN-4 | DEN-1 | DEN-2 | DEN-3 | DEN-4 |
| 2001 | AP545 | CYD-1,2 | CYD-1,2 | 20 | 25 | — | 50 | 40 | 50 | — | 319 |
| | AO949 | in one | in one | 20 | — | — | 20 | 319 | 20 | 13 | 100 |
| | AP335 | arm | arm | 20 | — | — | 252 | 100 | 16 | 10 | 200 |
| | AP817 | CYD-3,4 | CYD-3,4 | 20 | 16 | 32 | 40 | 319 | 25 | 32 | 402 |
| | geometric<br>mean | in the<br>other<br>arm | in the<br>other<br>arm | 20 | 10 | 8 | 56 | 142 | 25 | 12 | 225 |

TABLE 3-continued

SN50 neutralizing titer (units 1/dil)

| | Monkeys | | | | | | | | | | |
|---|---|---|---|---|---|---|---|---|---|---|---|
| | | Immunizations | | D + 28 | | | | D58 + 28 | | | |
| Group | ID | D0 | D58 | DEN-1 | DEN-2 | DEN-3 | DEN-4 | DEN-1 | DEN-2 | DEN-3 | DEN-4 |
| 2402 | AP676 | CYD- | CYD- | 63 | — | — | 126 | 100 | — | — | 40 |
| | AQ005 | 1,2,3,4 | 1,2,3,4 | 25 | — | — | 63 | 50 | — | — | 63 |
| | AP961 | | | 50 | — | — | 158 | 80 | — | 80 | 400 |
| | AN073AQ163 | | | 63 | — | — | 40 | 100 | — | 16 | 252 |
| | geometric mean | | | 47 | <10 | <10 | 84 | 80 | <10 | 13 | 126 |

—: titer < 10

TABLE 4

Viremia analysis (units: log 10 GEQ/ml)

| | | Primary immunization | | | | | | | | Booster | | | | | |
|---|---|---|---|---|---|---|---|---|---|---|---|---|---|---|---|
| Group | Monkey | D2 | D3 | D4 | D6 | D7 | D8 | D9 | D10 | D58 | D59 | D62 | D63 | D64 | D65 | D66 |
| 1 | AP545 | 3.17 | — | — | — | 3.12 | 3.67 | 4.55 | 4.59 | — | — | — | — | — | — | — |
| CYD1,2 + CYD3,4 | AO949 | 3.93 | 3.66 | 3.34 | 4.57 | — | — | — | — | — | — | — | — | — | — | — |
| 2 points of | AP335 | 3.36 | 3.06 | 3.34 | 3.83 | 4.05 | 4.41 | 4.24 | 3.64 | — | — | — | — | — | — | — |
| injection | AP817 | 4.17 | 3.99 | 3.61 | — | — | — | — | 2.89 | — | — | — | — | — | — | — |
| 2 | AP676 | — | — | — | — | — | — | — | 3.65 | — | — | — | — | — | — | — |
| CYD 1,2,3,4 | AQ005 | 3.19 | — | 3.35 | — | — | — | — | 3.41 | — | — | — | — | — | — | — |
| 1 point of | AP961 | — | — | — | — | 3.86 | 3.42 | 3.29 | 3.56 | — | — | — | — | — | — | — |
| injection | AQ163 | 3.18 | 3.16 | — | 3.30 | 3.60 | 2.95 | 3.00 | — | — | — | — | — | — | — | — |

Serotypes
CYD1
CYD2
CYD3
CYD4
CYD1 + 4

Briefly, the results can be summarized as follows:

The administration scheme according to the present invention makes it possible to qualitatively and quantitatively increase the homologous neutralizing antibody response which is obtained with the tetravalent immunization.

The bivalent immunization CYD-1,2 concomitant with a CYD-3,4 immunization carried out at a separate anatomical site induces, after booster, homologous responses against the four serotypes in all the monkeys, except for serotype 3 in one animal.

Furthermore, the responses against serotypes 1 and 4 have a tendency to be higher in the case of simultaneous bivalent immunizations than with tetravalent immunization at a single site.

The viremia (table 4) is predominantly caused by CYD-4 whether this is after simultaneous bivalent administration or tetravalent administration. It can therefore be concluded therefrom that separation of the serotypes does not promote the emergence of a serotype 1, 2 and 3 viremia.

The examples therefore show that the method of immunization according to the present invention improves the immunogenicity of the vaccinal dengue viruses without impairing the safety of the latter.

Example 2

Immunization by Simultaneous Injection of Two Bivalent Compositions CYD-1,4 and CYD-2,3 at Separate Anatomical Sites in Monkeys The viremia and the immunogenicity were tested in the monkey model as in example 1. In the present example, the bivalent compositions tested contain, respectively, the most immunogenic vaccinal viruses (CYD-1,4) and the least immunogenic vaccinal viruses (CYD-2,3).

2.1 Materials and Methods: Identical to Example 1

2.2 Evaluation of the Simultaneous Immunizations 2 groups of 4 monkeys of equivalent age and weight were immunized (see table 5).

The immunization was carried out as described in example 1.

TABLE 5

Composition of the groups and immunization protocol

| | Monkeys | |
|---|---|---|
| | Immunizations | |
| Group | D0 | D58 |
| 1 | CYD 1,4 in one arm | CYD 1,4 in one arm |
| | CYD 2,3 in the other arm | CYD 2,3 in the other arm |
| 2 | CYD 1,2,3,4 | CYD 1,2,3,4 |

The immunogenicity results obtained after one immunization (D28) and two immunizations (D86) are given in table 6.

The viremia results are similar to those obtained in example 1, showing a viremia induced by serotype 4 and no significant differences between the two groups.

TABLE 6

SN50 neutralizing titer (units 1/dil)

| Group | Monkeys ID | Immunizations D0 | Immunizations D58 | D0 + 28 DEN-1 | DEN-2 | DEN-3 | DEN-4 | D58 + 28 DEN-1 | DEN-2 | DEN-3 | DEN-4 |
|---|---|---|---|---|---|---|---|---|---|---|---|
| 1 | AR465 | CYD 1,2,3,4 | CYD 1,2,3,4 | 63 | 10 | < | 100 | 200 | 25 | 10 | 126 |
|   | AR558 |   |   | 13 | < | < | 126 | 401 | < | 20 | 160 |
|   | AR559 |   |   | < | < | < | 100 | 13 | < | < | 50 |
|   | AR639 |   |   | 25 | < | < | 318 | 201 | < | < | 201 |
|   | Geometric mean |   |   | 20 | < | < | 142 | 119 | < | < | 119 |
| 2 | AR083 | CYD 1,4 in one arm | CYD 1,4 in one arm | 63 | < | < | 201 | 100 | 16 | 10 | 126 |
|   | AR506 |   |   | 63 | 25 | 13 | 638 | 126 | 100 | 32 | 201 |
|   | AR610 | CYD 2,3 in the other arm | CYD 2,3 in the other arm | 63 | 20 | < | 100 | 159 | 50 | 40 | 253 |
|   | AR644 |   |   | 40 | < | < | 40 | 505 | 80 | 40 | 100 |
|   | Geometric mean |   |   | 56 | < | < | 150 | 178 | 50 | 27 | 159 |

<: titer < 10

The results support those obtained in example 1 and can be summarized as follows:

The administration scheme makes it possible to qualitatively and quantitatively increase the homologous neutralizing antibody response which is obtained with the tetravalent immunization.

The bivalent immunization CYD-1,4 concomitant with a CYD-2,3 immunization carried out at a separate anatomical site induces, after booster, homologous responses against the four serotypes in all the monkeys, which is not the case in the conventional tetravalent group, as seen in example 1.

Compared with those of the group of monkeys having received two bivalents CYD-1,2 and CYD-3,4 in example 1, the antibody titers observed after bivalent immunization CYD-1,4 concomitant with an immunization CYD-2,3 are higher for serotypes 1, 2 and 3 and lower for serotype 4, which shows a response that is better balanced between the 4 serotypes, with 4 being less dominant.

The separation of the dominant serotypes from the others in such an immunization scheme allowed a balanced response between the 4 serotypes to be obtained.

The two examples above therefore show that the method of immunization according to the present invention improves the immunogenicity of the vaccinal dengue viruses without impairing the safety of the latter as evaluated by measuring the viremia.

What is claimed is:

1. A method for inducing neutralizing antibodies against all 4 dengue serotypes, the method comprising:

(a) conducting a first series of administrations (i) of a dose of a vaccinal dengue virus of a first serotype and of a dose of a vaccinal dengue virus of a second serotype, and (ii) of a dose of a vaccinal dengue virus of a third serotype and of a dose of a vaccinal dengue virus of a fourth serotype, and (b) conducting a second series of administrations of doses (i) and (ii), in which the doses (i) and (ii) in (a) and (b) are administered simultaneously at separate anatomical sites, and in which the second series is implemented at least 30 days to at most 12 months after the first series.

2. The method as claimed in claim 1, in which the vaccinal dengue viruses (i) are administered in the form of a single bivalent dose.

3. The method as claimed in claim 1, in which the vaccinal dengue viruses (ii) are administered in the form of a single bivalent vaccinal dose.

4. The method as claimed in claim 1, in which said vaccinal dengue virus serotype 1 is selected from the group consisting of the VDV1 strain and of a CYD DEN-1.

5. The method as claimed in claim 1, in which said vaccinal dengue virus serotype 2 is selected from the group consisting of the VDV2 strain and of a CYD DEN-2.

6. The method as claimed in claim 1, in which said vaccinal dengue virus serotype 1 is the VDV1 strain and said vaccinal dengue virus serotype 2 is the VDV2 strain.

7. The method as claimed in claim 1, in which said vaccinal dengue virus serotype 1 is a CYD DEN-1 and said vaccinal dengue virus serotype 2 is a CYD DEN-2.

8. The method as claimed in claim 1, in which said vaccinal dengue virus serotype 3 is a CYD DEN-3.

9. The method as claimed in claim 1, in which said vaccinal dengue virus serotype 4 is a CYD DEN-4.

10. The method as claimed in claim 1, in which the first and second serotypes are, respectively, CYD DEN-1 and CYD DEN-2 and the third and fourth serotypes are, respectively, CYD DEN-3 and CYD DEN-4.

11. The method as claimed in claim 1, in which the amount of dengue vaccinal viruses serotypes 1, 2, 3 and 4 is within a range of from $10^3$ to $10^6$ $CCID_{50}$.

12. The method as claimed in claim 1, in which the vaccinal viruses used in the second series of administrations are identical to those used in the first series of administrations.

13. The method as claimed in claim 1, in which the second series of administrations is implemented 30 days to 60 days after the first series of administrations.

* * * * *